United States Patent [19]

Tsutsumi et al.

[11] 4,305,961
[45] Dec. 15, 1981

[54] COSMETIC COMPOSITION

[75] Inventors: Hisao Tsutsumi, Miyashiro; Junichi Kawano, Sakura; Shigeo Inoue, Ichikai, all of Japan; Shizuo Hayashi, deceased, late of Sugito, Japan, by Horuko Hayashi, legal representative

[73] Assignee: Kao Soap Co., Ltd., Tokyo, Japan

[21] Appl. No.: 78,046

[22] Filed: Sep. 24, 1979

[30] Foreign Application Priority Data

Sep. 28, 1978 [JP] Japan .................. 53-119723

[51] Int. Cl.³ .................. A61K 7/027; A61K 7/48
[52] U.S. Cl. .................. 424/361; 424/63; 424/168; 424/359
[58] Field of Search ............ 424/361; 536/115, 116, 536/119

[56] References Cited

U.S. PATENT DOCUMENTS

| | | | |
|---|---|---|---|
| 2,422,633 | 6/1947 | Petersen | 536/119 |
| 2,450,079 | 9/1948 | Brown | 536/116 |
| 2,626,257 | 1/1953 | Caldwell et al. | 424/69 |
| 2,626,935 | 1/1953 | DeGroote | 536/116 |
| 2,908,681 | 10/1959 | Anderson et al. | 536/116 |
| 3,102,114 | 8/1963 | Komori et al. | 536/116 |
| 3,972,997 | 8/1976 | Nakashio et al. | 424/69 |
| 4,032,702 | 6/1977 | James | 536/115 |

*Primary Examiner*—Dale R. Ore
*Attorney, Agent, or Firm*—Oblon, Fisher, Spivak, McClelland & Maier

[57] ABSTRACT

A cosmetic composition comprising as an essential ingredient a hydroxyalkyl-etherified glycolipid ester represented by the formula,

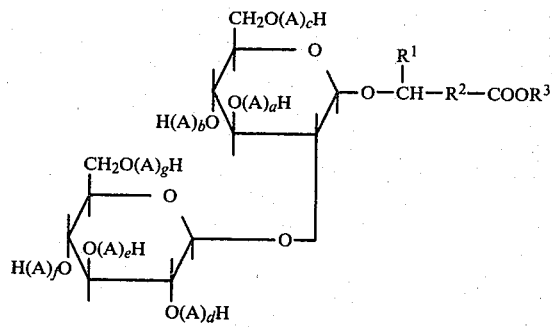

wherein $R^1$ represents a methyl group or a hydrogen atom; $R^2$ represents a saturated or unsaturated hydrocarbon group having 11 to 15 carbon atoms when $R^1$ is a methyl group, or a saturated or unsaturated hydrocarbon group having 12 to 16 carbon atoms when $R^1$ is a hydrogen atom; A represents $-CH_2CH_2O-$ or $-CH_2CH_2O-$ and

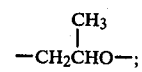

$R^3$ represents a saturated or unsaturated hydrocarbon group having 1 to 20 carbon atoms; and a,b,c,d,e,f,g and h are each integers, whose sum ranges from 1 to 100.

5 Claims, No Drawings

COSMETIC COMPOSITION

BACKGROUND OF THE INVENTION

1. Field of the Invention

This invention relates to cosmetics, more particularly to a novel cosmetic composition using a specific type of ester compound or hydroxyalkyl-etherified glycolipid ester.

2. Description of the Prior Art

It has been a conventional practice to incorporate a certain class of ingredients called a moisturizer or moisture barrier in general terms into cosmetics such as milky lotions, creams, beauty washes, dentifrice and like articles. The moisturizer is intended primarily to prevent those cosmetics from drying so that the moisture content in the cosmetics may be kept substantially constant during storage and usage. Another function of such moisturizer is to retain the skin moisture in a proper degree and hence render the skin freshlooking.

Known and used as the moisturizer in the art are polyalcohols such as propylene glycol, 1,3-butylene glycol, glycerine, polyglycerine, sorbitol and the like. These polyalcohols themselves have a hygroscopic property and exhibit a moisture-retaining activity due to its strong hydration with water, and therefore, act as a good moisturizer. However, difficulty is encountered in that when employed in cosmetics especially for use in skin treatment, the polyalcohols lend an excessive hygroscopic quality to the cosmetics. Because of less adaptability to the skin, the cosmetics thus prepared become objectionably oily and sticky to the skin and give an unpleasant finishing touch to the skin. Addition of the polyalcohols to the cosmetics in large amounts causes the moisture to be evaporated or escaped from inside of the skin, thereby resulting in chapped skin. Consequently, such polyalcohols can still not be satisfactory as a moisturizer for skin treatment cosmetics.

In view of the above noted difficulties, the present inventors have made intensive studies on a variety of compounds which can overcome these difficulties and which impart a pleasant finishing touch or good performance to the skin, coupled with an excellent moisture-retaining activity. As a result of these studies, it has been found that a hydroxyalkyl-etherified glycolipid ester meets with the desired properties and give the best results. Based upon this finding, the present invention has been accomplished.

SUMMARY OF THE INVENTION

Briefly stated, this invention provides a cosmetic composition comprising as an essential ingredient a hydroxyalkyl-etherified glycolipid ester represented by the formula (I),

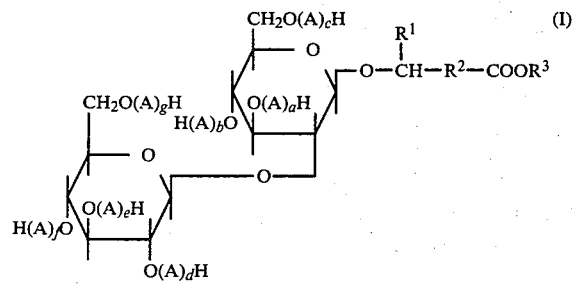

wherein $R^1$ represents a methyl group or a hydrogen atom; $R^2$ represents a saturated or unsaturated hydrocarbon group having 11 to 15 carbon atoms when $R^1$ is a methyl group, or a saturated or unsaturated hydrocarbon group having 12 to 16 carbon atoms when $R^1$ is a hydrogen atom; A represents $-CH_2CH_2O-$ or $-CH_2CH_2O-$ and

$R^3$ represents a saturated or unsaturated hydrocarbon group having 1 to 20 carbon atoms; and a, b, c, d, e, f, g and h are each integers, whose sum ranges from 1 to 100.

DETAILED DESCRIPTION OF THE PREFERRED EMBODIMENTS

A hydroxyalkyl-etherified glycolipid ester (hereinafter abbreviated as "EOPO-SL") which is useful in the invention can be produced, for instance, by subjecting glycolipid or its ester represented by the formula (II),

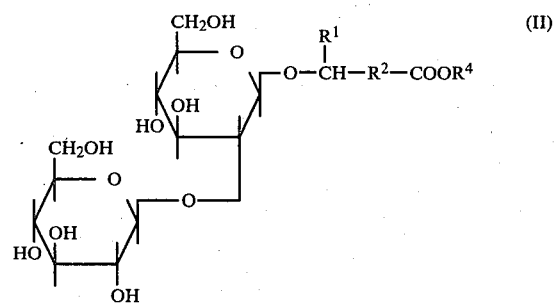

wherein $R^4$ represents a saturated or unsaturated hydrocarbon group having 1 to 20 carbon atoms or a hydrogen atom, and $R^1$ and $R^2$ are the same as defined above, to a reaction with or addition to ethylene oxide in the presence of an alkali catalyst; subsequently subjecting the reaction product or adduct to a reaction with or addition to propylene oxide; and finally subjecting the resulting reaction product or adduct to a further reaction with ethylene oxide.

The total number of carbon atoms in $R^1$ and $R^2$ of EOPO-SL in the formula (I) should be in the range of 12 to 16, and the ratio of

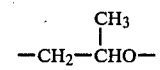

to $-CH_2-CH_2O-$ (hereinafter referred to as "addition mole ratio") in the range of 0 to 1. Outside these ranges results in reduced moisture-retaining activity of EOPO-SL because of its lowered solubility in water. Moreover, the addition mole number of alkylene oxide (a-h) should be in the range of 1 to 100, preferably 4 to 60. Beyond this range induces a rough feeling which adversely affects the desired finishing touch.

In general, EOPO-SL is a compound which is readily soluble in water and has good compatibility with waxes and oils. When coated or applied to the skin, EOPO-SL based cosmetics give a somewhat heavy feeling but do not become sticky and impart a dry and smooth finishing touch to the skin since such cosmetics are rather quick-drying.

The properties of EOPO-SL which is useful in and typical of the invention are shown in Table 1.

no water for reason of the fact that in addition to its good compatibility with oils, EOPO-SL possesses a hydrophilic property and hence has affinity for the moisture arising from the inside of the skin.

TABLE 1

| $R^1$ | $R^2$ | $R^3$ | Additives | Addition ratio* | Addition mole ratio | Appearance | Hydroxy value | Saponi- fication value | Acid value |
|---|---|---|---|---|---|---|---|---|---|
| $CH_3$ | $C_{15}H_{28}$ | $CH_3$ | Ethylene oxide | — | 5 | Yellowish brown viscous liquid | 463.5 | 67.0 | 0.5 |
| " | " | " | " | — | 15 | Yellowish brown viscous liquid | 311.3 | 45.2 | 0.7 |
| " | " | " | " | — | 30 | Yellowish brown viscous liquid | 205.8 | 30.0 | 0.7 |
| $CH_3$ | $C_{15}H_{28}$ | $CH_3$ | Ethylene oxide + propylene oxide | 1 | 30 | Yellowish brown viscous liquid | 181.7 | 28.6 | 0.3 |
| " | " | " | Ethylene oxide + propylene oxide | ½ | 30 | Yellowish brown viscous liquid | 196.5 | 28.9 | 1.2 |
| " | " | " | Ethylene oxide + propylene oxide | ⅔ | 60 | Yellowish brown paste | 125.7 | 19.5 | 0.7 |
| " | " | " | Ethylene oxide + propylene oxide | ¼ | 60 | Yellowish brown paste | 136.2 | 21.7 | 0.5 |

*Addition ratio:
Ratio of $-CH_2CHO-$ to $-CH_2-CH_2O-$ in $(A)a–(A)h$ in the formula (I)

The cosmetic composition according to the invention can be produced in the usual manner known in the art, except that the moisturizer present in any conventional cosmetics is wholly or partially replaced by EOPO-SL. In such instance, it is preferable that EOPO-SL be added in amounts of 0.1 to 100% by weight of the composition. Other desirable additives or ingredients which have been widely employed in the cosmetics may be used in combination with EOPO-SL and which include, for example, various oils, surface active agents, alcohols, viscosity modifiers, preservatives, drugs or chemicals, pigments, perfumes, humectants and water.

Suitable oils which are useful in the invention include liquid paraffin, vaseline, paraffin wax, squalane, ceresine wax, bees wax, specmaceti, carnauba wax, hydrogenated castor oil, olive oil, tsubaki oil, lanolin, lanolin alcohol, lanolin fatty acids, higher alcohols, fatty acids, synthetic ester oils of higher alcohols and fatty acids and the like. Suitable surface active agents include polyoxyethylene alkyl ethers, polyoxyethylene fatty acid esters, polyoxyethylene sorbitan fatty acid esters, sorbitan fatty acid esters, glycerine fatty acid esters, polyoxyethylene glycerine fatty acid esters, polyoxyethylene hydrogenated castor oil, polyoxyethylene sorbitol fatty acid esters, polyoxyethylene-polyoxypropylene condensates and the like. Suitable alcohols include ethanol, isopropanol and the like. Suitable viscosity modifiers include carboxylmethyl cellulose, methyl cellulose, hydroxyethyl cellulose, polyvinyl alcohol, polyvinylpyrrolidone, tragacanth gum, carrageenan, locust been gun, dextrin, dextrin fatty acid esters, carboxylvinyl polymer, gelatin, sodium alginate, acacia and the like. Suitable humectants include sorbitol, glycerine, propylene glycol, 1,3-butylene glycol, sodium pyrrolidonecarbonate, lactic acid, sodium lactate, polyethylene glycol and the like. Suitable preservatives include p-hydroxybenzoic acid alkyl esters, sodium benzoate, potassium sorbate, phenoxyethanol and the like. Further, suitable drugs or chemicals include vitamines, anti-inflammatory agents and germicides.

The cosmetic composition according to the invention is particularly useful in cosmetics including water as one of the ingredients. The present composition can also be satisfactorily used in cosmetics comprising sustantially Typical examples of the water-containing cosmetics are hand creams, cleansing creams, cold creams, vanishing creams, hair creams, milky lotions, beauty washes, shampoos, hair rinses, dentifrice, facial packs, foundation creams and the like. Typical examples of the water-free cosmetics are lip rouge, face powder, nail color eye-shadow, soaps, pomade, stick-shaped hair cosmetics and the like.

This invention will now be described in further detail with reference to some non-limiting Examples. The following Reference Example is merely illustrative of the preparation of EOPO-SL which is useful in the invention.

REFERENCE EXAMPLE (1) To a mixture of 1500 g of glucose, 75 g of a yeast extract and 15 g of urea was added water in an amount sufficient to adjust the whole volume to 15 l, and the resulting mixture was sterilized and utilized as a fermentation liquid. To this fermentation liquid was inoculated *Torulopsis bombicola* which had been cultured in a culture medium of the same composition as the fermentation liquid at 30° C. for 48 hours. The fermentation was carried out under the following conditions: temperature, 20° C.; stirring, 300 rpm; and aeration, 0.33 VVM. The fermentation was first conducted for 24 hours after the inoculation of the microorganisms, and beef tallow was added in an amount of 150 g and then added in the same amount at intervals of 24 hours. The added beef tallow amounted to 900 g. After the final addition, the fermentation was continued for further 24 hours. The fermentation time totaled 168 hours. The sophorolipid layer which had precipitated at the bottom of a fermentator was collected by decantation and filtration to give 1300 g of sophorolipid which was in the form of a paste having a water content of about 50%.

(2) 100 g of the thus obtained sophorolipid together with 2.5 g of polypropylene glycol having an average molecular weight of 200 was placed in a 200 ml round bottom flask equipped with a stirrer and a Liebig condenser. The mixture was evaporated with stirring at 80° C. in an oil bath under a reduced pressure of 250 mmHg to eliminate water. About 2 hours later, the distillation of water was completed, and the water content at this time was found to be less than 1%.

(3) To the thus obtained sophorolipid-polypropylene glycol solution were added 150 g of methanol and then 2.5 g of sulfuric acid, and the resulting mixture was reacted at 40±2° C. for 90 minutes. The reaction was regarded as having reached completion when many spots shown by the raw material or sophorolipid converged on one spot corresponding to a glycolipid methyl ester by thin-layer chromatography on silica gel [developing solvent: chloroform-methanol-acetic acid (75:20:5)].

After the completion of the reaction, the mixture was filtered, followed by neutralization with a given amount of potassium hydroxide. The filtrate was again placed in a round bottom flask equipped with a Liebig condenser, and methanol and methyl acetate which had been formed were removed by distillation to obtain 48 g of a mixture containing 94% of a [(2'-O-β-D-glucopyranosyl-β-D-glucopyranosyl)oxy]alkanic acid or alkenic acid methyl ester as a brown paste in which polypropylene glycol coexisted. This mixture was purified by column chromatography on silica gel, thereby yielding a pure [2'-O-β-D-glucopyranosyl-β-D-glucopyranosyl)oxy]alkanic acid and alkenic acid methyl ester.

IR $(cm^{-1})$:1740 (>C=O ester); 1380-3200 (—OH sugar); 900-750 (glucopyranose ring).

NMR[δ(pyridine)]:1.1-1.6 (—$CH_2$—$CH_2$—); 3.6 (—O—$CH_3$); 3.5-5.0 (sugar); 5.5 (—CH=CH— unsaturated fatty acid).

| Oil Characterization Analyses: | |
|---|---|
| Acid value | 0 |
| Hydroxy valud: | 615 |
| Saponification value: | 88 |
| Ester value: | 87 |

(4) When 1 mole of this produce was decomposed in a 5N hydrochloric acid-methanol solution and then subjectd to gas chromatography, it was found that 2 moles of methylglucoxide and 1 mole of a hydroxyfatty acid methyl ester were produced. In an acutoclave was placed 100 g of the thus obtained mixture of the [(2'-O-β-D-glucopyranosyl-β-D-glucopyranosyl)oxy]alkanic acid and alkenic acid methyl ester and coexisting polypropylene glycol together with 0.25 g of potassium hydroxide. The resulting mixture was reacted at 100°-120° C. while propylene oxide gas and ethylene oxide gas were being blown in turn into the mixture in amounts corresponding to given addition mole numbers. After the completion of the reaction, the mixture was neutralized with phosphoric acid and filtered under high pressure to obtain a crude product in the form of a brown paste. This product was purified by column chromatography on silica gel, thereby yielding a pure polyoxyethylene-polyoxypropylene[(2'-O-β-D-glucopyranosyl-β-D-glucopyranosyl)oxy]alkanic acid and alkenic acid methyl ester as a pale yellow paste.

EXAMPLE 1

Several test creams were prepared using EOPO-SL and comparative compounds as a moisturizer and having the formulation indicated below. Each test cream was placed in a weighing bottle having a diameter of 30 mm, and the bottle was allowed to stand uncapped or opened at an ambient temperature of 40° C. and a relative humidity of 30%. Any varying decreases in weight of the test creams after the standing were measured and compared by the moisture-retaining percentage, with the results tabulated in Table 2.

| Cream Formulation | |
|---|---|
| Test compound or moisturizer | 10% |
| Stearic acid | 3% |
| Liquid paraffin | 7% |
| Bees wax | 2% |
| Polyoxethylene stearate | 1.5% |
| Stearic acid monoglyceride | 1.5% |
| Methylparaben | 0.1% |
| Butylparaben | 0.1% |
| Purfume | 0.2% |
| Purified water | balance |
| | (% by weight) |

TABLE 2

| | Test compounds | | | | | Moisture-retaining percentage (%) | | |
|---|---|---|---|---|---|---|---|---|
| | | $R^1$ | $R^2$ | $R^3$ | Addition mole number | Addition ratio | After 1 day | After 3 days | After 10 days |
| Present compounds | EOPO-SL | $CH_3$ | $C_{15}H_{28}$ | $CH_3$ | 10 | 0 | 99.9 | 97.5 | 91.3 |
| | | $CH_3$ | $C_{15}H_{28}$ | $CH_3$ | 30 | ⅔ | 100.0 | 98.8 | 96.5 |
| | | H | $C_{14}H_{26}$ | $C_{12}H_{25}$ | 30 | ¼ | 99.5 | 93.2 | 86.8 |
| | | H | $C_{14}H_{26}$ | $(A)_hH$ | 5 | 1/9 | 100.0 | 98.5 | 93.5 |
| | Glycerine | | | | | | 99.5 | 93.5 | 90.2 |
| | Propylene glycol | | | | | | 97.5 | 93.5 | 87.4 |
| Comparative | Sorbitol | | | | | | 96.4 | 92.3 | 85.4 |
| compounds | Polyglycerine | | | | | | 93.2 | 88.6 | 80.4 |
| | 1,3-butan diol | | | | | | 90.4 | 83.2 | 72.6 |
| Control | Not Added | | | | | | 85.4 | 72.3 | 54.1 |

Note:
The moisture-retaining percentage was calculated according to the following equation.

$$\text{Moisture-retaining percentage (\%)} = \frac{\text{Weight of cream after standing}}{\text{Weight of cream before standing}} \times 100$$

From the results obtained above, the creams embodying the invention were found to be extremely excellent in the moisture-retaining activity.

EXAMPLE 2

Several test milky lotions were prepared using EOPO-SL and comparative compounds as a moisturizer and having the formulation indicated below. The finishing touch or performance of these milky lotions was marked and scored by ten panelists, with the results tabulated in Table 3.

| Milky Lotion Formulation | |
|---|---|
| Test compound or moisturizer | 7.0% |
| Ethanol | 15.0% |

| Milky Lotion Formulation | |
|---|---|
| Glycin | 1.0% |
| Polyoxyethylene cetyl ether | 1.5% |
| Sodium pyrrolidone carbonate | 1.0% |
| Perfume | 0.2% |
| Water | balance |
| | (% by weight) |

TABLE 3

| | Test compounds | | | Addition mole number | Addition ratio | Stickness | Moistness | Spreadability | Refreshness |
|---|---|---|---|---|---|---|---|---|---|
| | | $R^1$ | $R^2$ | $R^3$ | | | | | |
| Present compounds | EOPO-SL | $CH_3$ | $C_{15}H_{28}$ | $CH_3$ | 10 | 0 | −1.5 | +1.8 | +1.3 | +1.9 |
| | | $CH_3$ | $C_{15}H_{28}$ | $CH_3$ | 30 | 1 | −1.0 | +1.7 | +1.7 | +1.8 |
| Comparative compounds | Glycerine | | | | | | +1.3 | +0.3 | −0.7 | −1.5 |
| | Sorbitol | | | | | | +0.3 | −1.0 | −0.3 | +0.2 |
| | Propylene glycol | | | | | | +0.1 | +0.1 | +0.3 | −0.1 |

Note:
Each touch or performance was adjudged according to the following evaluation standards. The numerals are expressed as the average values of the ten panelists' scores.
Severe +2
Fairly +1
Moderate 0
Lacking −1
Nothing −2

From the results obtained above, the beauty washes comprising EOPO-SL were found to give less sticky and more moist feeling to the skin than did the beauty washes including conventional moisturizers.

EXAMPLE 3

Hand Cream

| Starting Materials | | |
|---|---|---|
| (1) | EOPO-SL ($R^1 = CH_3$, $R^2 = C_{15}H_{28}$, $R^3 = CH_3$, a − h = 10, addition mole ratio = 0 | 5.5% |
| (2) | Stearic acid | 10.0% |
| (3) | Stearic acid monoglyceride | 1.5% |
| (4) | Triethanolamine | 0.3% |
| (5) | Preservative (Sodium benzoate) | 0.2% |
| (6) | Antioxidant (Butyl hydroxy toluene) | 0.05% |
| (7) | Perfume | 0.2% |
| (8) | Purified water | balance |
| | | (% by weight) |

PREPARATION (1) to (6) and (8) were mixed at 70° C., and the mixture was emulsified. After the completion of the emulsification, the mixture was cooled and then subjected to the addition of (7) to produce a hand cream.

EXAMPLE 4

Cleansing Milk (Milky Lotion)

| Starting Materials | | |
|---|---|---|
| (1) | EOPO-SL ($R^1 = CH_3$, $R^2 = C_{15}H_{28}$, $R^3 = CH_3$, a − h = 30, addition mole ratio = 2:3 | 5.0% |
| (2) | Liquid paraffin | 1.5% |
| (3) | Specmacetic | 1.5% |
| (4) | Cetanol | 0.5% |
| (5) | Sorbitan monooleate | 1.0% |
| (6) | Polyoxyethylene sorbitan monooleate | 0.5% |
| (7) | Preservative (Methylparabene) | 0.1% |
| (8) | Antioxidant (Butyl hydroxy toluene) | 0.1% |
| (9) | Perfume | 0.2% |
| (10) | Purified water | balance |

| Starting Materials | |
|---|---|
| | (% by weight) |

PREPARATION (2) to (6) were mixed at 70° C., and to this mixture was added with stirring an admixture of (1), (7), (8) and (10) which had been heated at 70° C. The resulting mixture was emulsified. After the completion of the emulsification, the mixture was cooled and then subjected to the addition of (9) to produce a cleansing milk.

EXAMPLE 5

Skin Lotion

| Starting Materials | | |
|---|---|---|
| (1) | EOPO-SL ($R^1 = H$, $R^2 = C_{14}H_{26}$, $R^3 = C_{12}H_{25}$, a − h = 40, addition mole ratio = 1:9 | 5.0% |
| (2) | Ethanol | 15.0% |
| (3) | L-serine | 1.0% |
| (4) | Polyoxyethylene oleyl ether | 1.5% |
| (5) | Perfume | 0.2% |
| (6) | Purified water | balance |
| | | (% by weight) |

PREPARATION (1) to (6) were mixed and stirred to make a mixture homogeneous, thereby producing a skin lotion.

EXAMPLE 6

Facial Pack

| Starting Materials | | |
|---|---|---|
| (1) | EOPO-SL ($R^1 = CH_3$, $R^2 = C_{15}H_{28}$, $R^3 = CH_3$, a − h = 8, addition mole ratio = 1 | 3.0% |
| (2) | Polyvinyl alcohol | 12.5% |
| (3) | Ethylene glycol | 2.5% |
| (4) | Methylparaben | 0.1% |
| (5) | Titanium dioxide | 1.5% |
| (6) | Perfume | 0.2% |
| (7) | Purified water | balance |
| | | (% by weight) |

PREPARATION (1) to (5) and (7) were mixed at 90° C. The mixture was cooled and then subjected to the addition of (6) to produce a facial pack.

EXAMPLE 7

Lip Stick

| | Starting Materials | |
|---|---|---|
| (1) | EOPO-SL ($R^1$ = $CH_3$, $R^2$ = $C_{15}H_{28}$, $R^3$ = $CH_3$, a — h = 15, addition mole ratio = 1:4 | 6.0% |
| (2) | Carnauba wax | 5.0% |
| (3) | Bees wax | 15.0% |
| (4) | Ceresine wax | 15.0% |
| (5) | Castor oil | 40.3% |
| (6) | Oleyl alcohol | 14.0% |
| (7) | Titanium dioxide | 3.0% |
| (8) | Red iron oxide | 1.0% |
| (9) | Red pigment | 0.5% |
| (10) | Perfume | 0.2% |
| | | (% by weight) |

PREPARATION (1) to (9) were mixed at 85°–90° C. to make a mixture homogeneous. After being allowed to cool to 70° C., the mixture was subjected to the addition of (10). Thereafter, the resulting mixture was cast into a mold and cooled to produce a lip stick.

What is claimed is:

1. In an aqueous cosmetic composition for the treatment of skin and hair, the improvement comprising the addition of from 0.1 to 100% by weight of the composition, as the moisturizing component, of a hydroxyalkyl-etherified glycolipid ester represented by the formula,

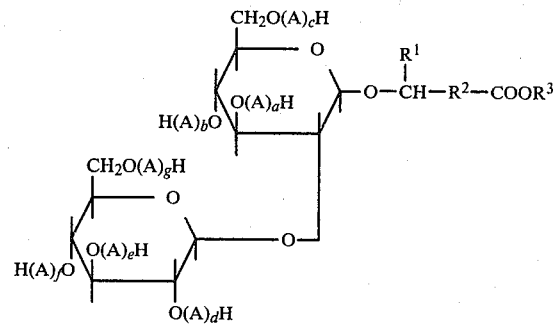

wherein $R^1$ represents a methyl group or a hydrogen atom; $R^2$ represents a saturated or unsaturated hydrocarbon group having 11 to 15 carbon atoms when $R^1$ is a methyl group, or a saturated or unsaturated hydrocarbon group having 12 to 16 carbon atoms when $R^1$ is a hydrogen atom; A represents —$CH_2CH_2O$— or combined with

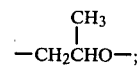

$R^3$ represents a saturated or unsaturated hydrocarbon group having 1 to 20 carbon atoms; and a, b, c, d, e, f, g, and h are each integers, whose sum ranges from 1 to 100.

2. A cosmetic composition according to claim 1, wherein $R^1$ and $R^2$ have a total numbr of carbon atoms in the range of 12 to 16.

3. A cosmetic composition according to claim 1, wherein the ratio of

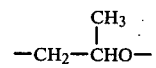

to —$CH_2$—$CH_2O$— is in the range of 0 to 1.

4. A cosmetic composition according to claim 1, wherein a, b, c, d, e, f, g and h are each integers, whose sum ranges from 4 to 60.

5. A composition according to claim 1, wherein there is added 10% of the hydroxyalkyl-etherified glycolipid ester.

* * * * *